(12) United States Patent
Neidlein et al.

(10) Patent No.: US 6,506,708 B1
(45) Date of Patent: Jan. 14, 2003

(54) 3-(HETEROCYCLYL)-BENZOYLPYRAZOLE-DERIVATIVES

(75) Inventors: Ulf Neidlein, Mannheim (DE); Norbert Götz, Worms (DE); Ulf Misslitz, Neustadt (DE); Roland Götz, Neulussheim (DE); Ernst Baumann, Dudenhofen (DE); Wolfgang von Deyn, Neustadt (DE); Steffen Kudis, Mannheim (DE); Klaus Langemann, Worms (DE); Guido Mayer, Neustadt (DE); Matthias Witschel, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/857,034

(22) PCT Filed: Dec. 2, 1999

(86) PCT No.: PCT/EP99/09412

§ 371 (c)(1), (2), (4) Date: May 31, 2001

(87) PCT Pub. No.: WO00/34272

PCT Pub. Date: Jun. 15, 2000

(30) Foreign Application Priority Data

Dec. 4, 1998 (DE) .......................... 198 55 850
Aug. 6, 1999 (DE) .......................... 199 36 705

(51) Int. Cl.[7] .................. A01N 43/56; A01N 43/80; C07D 231/20; C07D 413/10
(52) U.S. Cl. ................. 504/282; 548/240; 548/365.1
(58) Field of Search ............. 548/365.1, 240; 504/282

(56) References Cited

U.S. PATENT DOCUMENTS 5,846,907 A 12/1998 von Deyn et al.
6,147,031 A 11/2000 Addachi et al.
6,165,944 A 12/2000 von Deyn et al.

FOREIGN PATENT DOCUMENTS

| CA | 2278331 | 1/1998 |
| WO | WO 96/26206 | 8/1996 |
| WO | WO 98/31681 | 7/1998 |
| WO | WO 98/31682 | 7/1998 |

Primary Examiner—Robert W. Ramsuer
(74) Attorney, Agent, or Firm—Keil & Weinkauf

(57) ABSTRACT

3-(Heterocyclyl)benzoylpyrazole derivatives of the formula I

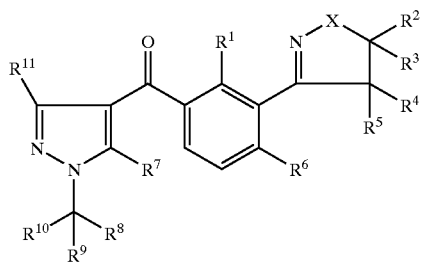

where:

X is O, NH or N-alkyl;

$R^1$ is nitro, halogen, alkoxy, haloalkoxy, alkylthio, haloalkylthio, alkylsulfonyl or haloalkylsulfonyl;

$R^2, R^3, R^4, R^5$ are hydrogen, alkyl or haloalkyl;

$R^6$ is halogen, nitro, haloalkyl, alkoxy, haloalkoxy, alkylthio, haloalkylthio, alkylsulfonyl or haloalkylsulfonyl;

$R^7$ is hydroxyl, alkoxy, alkenyloxy, alkylsulfonyloxy, alkylcarbonyloxy, (alkylthio)carbonyloxy, phenylsulfonyloxy or phenylcarbonyloxy, where the phenyl radical may be substituted;

$R^8, R^9$ are alkyl;

$R^{10}$ is hydrogen or alkyl;

$R^{11}$ is hydrogen or alkyl;

and their agriculturally useful salts, compounds for their preparation, and the use of these compounds or of compositions comprising them for controlling undesirable plants are described.

10 Claims, No Drawings

3-(HETEROCYCLYL)-BENZOYLPYRAZOLE-DERIVATIVES

The present invention relates to 3-(heterocyclyl) benzoylpyrazole derivatives of the formula I

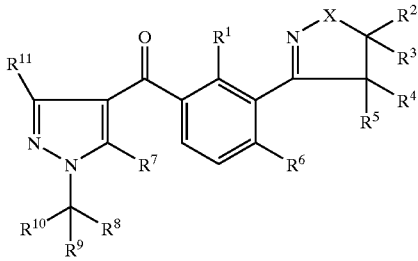

where:
X is O, NH or N(C$_1$–C$_6$-alkyl);
R$^1$ is nitro, halogen, C$_1$–C$_4$-alkoxy, C$_1$–C$_4$-haloalkoxy, C$_1$–C$_4$-alkylthio, C$_{1-C4}$-haloalkylthio, C$_1$–C$_4$-alkylsulfonyl or C$_1$–C$_4$-haloalkylsulfonyl;
R$^2$,R$^3$,R$^4$,R$^5$ are hydrogen, C$_1$–C$_4$-alkyl or C$_1$–C$_4$-haloalkyl;
R$^6$ is halogen, nitro, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, C$_1$–C$_4$-alkylsulfonyl or C$_1$–C$_4$-haloalkylsulfonyl;
R$^7$ is hydroxyl, C$_1$–C$_6$-alkoxy, C$_3$–C$_6$-alkenyloxy, C$_1$–C$_6$-alkylsulfonyloxy, C$_1$–C$_6$-alkylcarbonyloxy, C$_1$–C$_4$-(alkylthio)carbonyloxy, phenylsulfonyloxy or phenylcarbonyloxy, where the phenyl radical of the two last-mentioned substituents may be partially or fully halogenated and/or may carry one to three of the following groups: nitro, cyano, C$_1$–C$_4$-alkyl, C$_1$–C$_4$-haloalkyl, C$_1$–C$_4$-alkoxy or C$_1$–C$_4$-haloalkoxy;
R$^8$,R$^9$ are C$_1$–C$_4$-alkyl;
R$^{10}$ is hydrogen or C$_1$–C$_4$-alkyl; where the number of the carbon atoms of the radicals R$^8$,R$^9$ and R$^{10}$ together is at most 7,
R$^{11}$ is hydrogen or C$_1$–C$_4$-alkyl;
and its agriculturally useful salts.

Moreover, the invention relates to processes for preparing compounds of the formula I, to compositions comprising them and to the use of these derivatives or of the compositions comprising them for controlling harmful plants.

Pyrazol-4-yl benzoyl derivatives are disclosed in the literature, for example in WO 96/26206 and WO 98/31681.

However, the herbicidal properties of the prior-art compounds and their compatibility with crop plants are not entirely satisfactory. It is an object of the present invention to provide novel, in particular herbicidally active, compounds having improved properties.

We have found that this object is achieved by the 3-(heterocyclyl)benzoylpyrazole derivatives of the formula I and their herbicidal action.

Furthermore, we have found herbicidal compositions which comprise the compounds I and have very good herbicidal action. Moreover, we have found processes for preparing these compositions and methods for controlling undesirable vegetation using the compounds I.

Depending on the substitution pattern, the compounds of the formula I may contain one or more chiral centers, in which case they are present as enantiomers or mixtures of diastereomers. The invention provides both the pure enantiomers or diastereomers and their mixtures.

The compounds of the formula I can also be present in the form of their agriculturally useful salts, the kind of salt usually being immaterial. In general, the salts of those cations or the acid addition salts of those acids are suitable whose cations and anions, respectively, do not adversely affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced here by C$_1$–C$_4$-alkyl, hydroxy-C$_1$–C$_4$-alkyl, C$_1$–C$_4$-alkoxy-C$_1$–C$_4$-alkyl, hydroxy-C$_1$–C$_4$-alkoxy-C$_1$–C$_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri(C$_1$–C$_4$-alkyl)sulfonium, and sulfoxonium ions, preferably tri(C$_1$–C$_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of C$_1$–C$_4$-alkanoic acids, preferably formate, acetate, propionate and butyrate.

The organic molecular moieties mentioned for the substituents R$^1$–R$^{11}$ or as radicals on phenyl rings are collective terms for individual enumerations of the individual group members. All hydrocarbon chains, i.e. all alkyl, alkylcarbonyl, haloalkyl, alkoxy, haloalkoxy, alkylcarbonyloxy, (alkylthio)carbonyloxy, alkylsulfonyloxy, alkylthio, haloalkylthio, alkylsulfonyl, haloalkylsulfonyl, alkenyl and alkenyloxy moieties can be straight-chain or branched. Unless indicated otherwise, halogenated substituents preferably carry one to five identical or different halogen atoms. The term "halogen" represents in each case fluorine, chlorine, bromine or iodine.

Examples of other meanings are:
C$_1$–C$_4$-alkyl, and the alkyl moieties of C$_1$–C$_4$-alkylcarbonyl and C$_1$–C$_4$-alkylcarbonyloxy: for example methyl, ethyl, propyl, 1-methylethyl, butyl, 1-methylpropyl, 2-methylpropyl and 1,1-dimethylethyl;

C$_1$–C$_6$-alkyl, and the alkyl moieties of C$_1$–C$_6$-alkylcarbonyl and C$_1$–C$_6$-alkylcarbonyloxy: C$_1$–C$_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

C$_1$–C$_4$-haloalkyl: a C$_1$–C$_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-difluoroethyl, 2,2,2- trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy: for example methoxy, ethoxy, propoxy, 1-methylethoxy, butoxy, 1-methylpropoxy, 2-methylpropoxy and 1,1-dimethylethoxy;

$C_1$–$C_6$-alkoxy: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylthio and the alkylthio moieties of $C_1$–$C_4$-(alkylthio)carbonyloxy: for example methylthio, ethylthio, propylthio, 1-methylethylthio, butylthio, 1-methylpropylthio, 2-methylpropylthio and 1,1-dimethylethylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_4$-alkylsulfonyl ($C_1$–$C_4$-alkyl-S(=O)$_2$–), and the alkylsulfonyl moieties of $C_1$–$C_4$-alkylsulfonyloxy: for example methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl, and the alkylsulfonyl moieties of $C_1$–$C_6$-alkylsulfonyloxy: a $C_1$–$C_4$-alkylsulfonyl radical as mentioned above, and also, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl and nonafluorobutylsulfonyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-3-en-1-yloxy, 1,2-dimethylbut-2-en-1-yloxy, 1,2-dimethylbut-3-en-1-yloxy, 1,3-dimethylbut-3-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-3-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl.

The phenyl rings are preferably unsubstituted or carry one to three halogen atoms and/or one nitro group, one cyano group, one or two methyl, trifluoromethyl, methoxy or trifluoromethoxy groups.

Emphasis is given to those compounds of the formula I where $R^7$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

Preference is given to the 3-(heterocyclyl)benzoylpyrazole derivatives of the formula I where:

X is O;

$R^1$ is nitro, halogen, $C_1$–$C_4$-alkoxy or $C_1$–$C_4$-alkylthio; particularly preferably nitro, halogen or $C_1$–$C_4$-alkoxy; with particular preference halogen, such as fluorine, chlorine or bromine, or $C_1$–$C_4$-alkoxy, such as methoxy or ethoxy; with very particular preference chlorine or methoxy;

$R^2, R^3, R^4, R^5$ are hydrogen, $C_1$–$C_4$-alkyl or $C_1$–$C_4$-haloalkyl; particularly preferably hydrogen, methyl, ethyl, propyl, 1-methylethyl, fluoromethyl or chloromethyl; with particular preference hydrogen, methyl, ethyl or chloromethyl;

$R^6$ is $C_1$–$C_4$-alkylthio or $C_1$–$C_4$-alkylsulfonyl; particularly preferably methylthio, ethylthio or 1-methyl-1-ethylthio, methylsulfonyl, ethylsulfonyl, 1-methylethylsulfonyl or propylsulfonyl; with particular preference methylsulfonyl, ethylsulfonyl, 1-methylethylsulfonyl or propylsulfonyl;

$R^7$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, $C_1$–$C_4$-(alkylthio)carbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl, $C_1$–$C_4$-alkoxy, $C_3$–$C_6$-alkenyloxy, $C_1$–$C_4$-alkylsulfonyloxy, $C_1$–$C_4$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

$R^8, R^9$ are $C_1$–$C_4$-alkyl; particularly preferably methyl, ethyl, propyl, 1-methyl-1-ethyl, butyl, 1-methyl-1-propyl and 2-methyl-1-propyl;

$R^{10}$ is hydrogen or $C_1$–$C_4$-alkyl; particularly preferably $C_1$–$C_4$-alkyl; with particular preference methyl, ethyl or propyl;

$R^{11}$ is hydrogen or $C_1$–$C_4$-alkyl; particularly preferably hydrogen or methyl.

Particular preference is given to the 3-(heterocyclyl)benzoylpyrazole derivatives of the formula I where X is O;

$R^1$ is halogen or $C_1$–$C_4$-alkoxy; particularly preferably halogen, such as fluorine, chlorine or bromine, or methoxy or ethoxy; with particular preference chlorine or methoxy;

$R^6$ is $C_1$–$C_4$-alkylsulfonyl; particularly preferably methylsulfonyl, ethylsulfonyl, 1-methyl-1-ethylsulfonyl or propylsulfonyl;

$R^7$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^8$,$R^9$ are $C_1$–$C_4$-alkyl;

$R^{10}$ is hydrogen or $C_1$–$C_4$-alkyl.

Very particular preference is given to the 3-(heterocyclyl)benzoylpyrazole derivatives of the formula I where $R^8$ is $C_2$–$C_4$-alkyl, for example ethyl, 1-methyl-1-ethyl, propyl or butyl;

$R^9$ is $C_1$–$C_4$-alkyl, for example methyl or ethyl;

$R^{10}$ is hydrogen or $C_1$–$C_4$-alkyl, for example methyl or ethyl.

Very particular preference is also given to the 3-(heterocyclyl)benzoylpyrazole derivatives of the formula I where $R^8$ is methyl;

$R^9$ is $C_1$–$C_4$-alkyl, for example methyl, ethyl, propyl or butyl;

$R^{10}$ is $C_1$–$C_4$-alkyl, for example methyl or ethyl.

Very particular preference is also given to the 3-(heterocyclyl)benzoylpyrazole derivatives of the formula I where $R^8$,$R^9$ are methyl;

$R^{10}$ is hydrogen.

Preference is also given to the 3-(heterocyclyl)benzoylpyrazole derivatives of the formula I where:

X is O $R^1$ is nitro, halogen, $C_1$–$C_4$-alkoxy or $C_1$–$C_4$-alkylthio; particularly preferably nitro, halogen or $C_1$–$C_4$-alkoxy; with particular preference halogen, such as fluorine, chlorine or bromine, or $C_1$–$C_4$-alkoxy, such as methoxy or ethoxy; with very particular preference chlorine or methoxy;

$R^2$,$R^3$,$R^4$,$R^5$ are hydrogen, $C_1$–$C_4$-alkyl or $C_1$–$C_4$-haloalkyl; particularly preferably hydrogen, methyl, ethyl, propyl, 1-methyl-1-ethyl, chloromethyl or fluoromethyl; with particular preference hydrogen, methyl, ethyl or chloromethyl;

$R^6$ is halogen, nitro, $C_1$–$C_4$-haloalkyl, $C_1$–$C_4$-alkoxy or $C_1$–$C_4$-haloalkoxy; particularly preferably halogen, such as chlorine or bromine, nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy, chlorodifluoromethoxy or trifluoromethoxy;

$R^7$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, $C_1$–$C_4$-(alkylthio)carbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl, $C_1$–$C_4$-alkoxy, $C_3$–$C_6$-alkenyloxy, $C_1$–$C_4$-alkylsulfonyloxy, $C_1$–$C_4$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

$R^8$,$R^9$ are $C_1$–$C_4$-alkyl; particularly preferably methyl, ethyl, propyl, 1-methyl-1-ethyl, butyl, 1-methyl-1-propyl and 2-methyl-1-propyl;

$R^{10}$ is hydrogen or $C_1$–$C_4$-alkyl; particularly preferably $C_1$–$C_4$-alkyl; with particular preference methyl, ethyl or propyl;

$R^{11}$ is hydrogen or $C_1$–$C_4$-alkyl; particularly preferably hydrogen or methyl.

Particular preference is given to the 3-(heterocyclyl)benzoylpyrazole derivatives of the formula I where X is O;

$R^1$ is halogen or $C_1$–$C_4$-alkoxy; particularly preferably halogen, such as fluorine, chlorine or bromine, or methoxy or ethoxy; with particular preference chlorine or methoxy;

$R^6$ is halogen, nitro, $C_1$–$C_4$-haloalkyl, $C_1$–$C_4$-alkoxy or $C_1$–$C_4$-haloalkoxy; particularly preferably halogen, such as chlorine or bromine, nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy;

$R^7$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^8$,$R^9$ are $C_1$–$C_4$-alkyl;

$R^{10}$ is hydrogen or $C_1$–$C_4$-alkyl.

Very particular preference is given to the 3-(heterocyclyl)benzoylpyrazole derivatives of the formula I where $R^8$ is $C_2$–$C_4$-alkyl, for example ethyl, 1-methyl-1-ethyl, propyl or butyl;

$R^9$ is $C_1$–$C_4$-alkyl, for example methyl or ethyl;

$R^{10}$ is hydrogen or $C_1$–$C_4$-alkyl, for example methyl or ethyl.

Very particular preference is also given to the 3-(heterocyclyl)benzoylpyrazole derivatives of the formula I where $R^8$ is methyl;

$R^9$ is $C_1$–$C_4$-alkyl, for example methyl, ethyl, propyl or butyl;

$R^{10}$ is $C_1$–$C_4$-alkyl, for example methyl or ethyl.

Very particular preference is also given to the 3-(heterocyclyl)benzoylpyrazole derivatives of the formula I where $R^8$,$R^9$ are methyl;

$R^{10}$ is hydrogen.

Preference is also given to the 3-(heterocyclyl)-substituted benzoylpyrazoles [sic] of the formula I where:

X is N($C_1$–$C_6$-alkyl); particularly preferably N-methyl, N-ethyl, N-(1-methyl-1-ethyl) or N-propyl;

$R^1$ is nitro, halogen, $C_1$–$C_4$-alkoxy or $C_1$–$C_4$-alkylthio; particularly preferably nitro, halogen or $C_1$–$C_4$-alkoxy; with particular preference halogen, such as fluorine, chlorine or bromine, or $C_1$–$C_4$-alkoxy, such as methoxy or ethoxy; with very particular preference chlorine or methoxy;

$R^2$,$R^3$,$R^4$,$R^5$ are hydrogen, $C_1$–$C_4$-alkyl or $C_1$–$C_4$-haloalkyl; particularly preferably hydrogen, methyl, ethyl, propyl, 1-methyl-1-ethyl, fluoromethyl or chloromethyl; with particular preference hydrogen, methyl, ethyl or chloromethyl;

$R^6$ is halogen, nitro, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl or $C_1$–$C_4$-haloalkylsulfonyl; particularly preferably halogen, such as fluorine, chlorine or bromine, nitro, $C_1$–$C_4$-haloalkyl, such as difluoromethyl or trifluoromethyl, $C_1$–$C_4$-alkoxy, such as methoxy or ethoxy, $C_1$–$C_4$-haloalkoxy, such as difluoromethoxy, chlorodifluoromethoxy or trifluoromethoxy, $C_1$–$C_4$-alkylthio, such as methylthio or ethylthio, or $C_1$–$C_4$-alkylsulfonyl, such as methylsulfonyl, ethylsulfonyl, 1-methyl-1-ethylsulfonyl or propylsulfonyl;

$R^7$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, $C_1$–$C_4$-(alkylthio)carbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl, $C_1$–$C_4$-alkoxy, $C_3$–$C_6$-alkenyloxy, $C_1$–$C_4$-alkylsulfonyloxy, $C_1$–$C_4$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

$R^8$,$R^9$ are $C_1$–$C_4$-alkyl; particularly preferably methyl, ethyl, propyl, 1-methyl-1-ethyl, butyl, 1-methyl-1-propyl and 2-methyl-1-propyl;

$R^{10}$ is hydrogen or $C_1$–$C_4$-alkyl; particularly preferably $C_1$–$C_4$-alkyl; with particular preference methyl, ethyl or propyl;

$R^{11}$ is hydrogen or $C_1$–$C_4$-alkyl; particularly preferably hydrogen or methyl.

Particular preference is given to the 3-(heterocyclyl)benzoylpyrazole derivatives of the formula I where $R^7$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl.

Preference is likewise given to the 3-(heterocyclyl)benzoyl-pyrazole derivatives of the formula I where the variables are as defined below:

X is O;

$R^1$ is halogen or $C_1$–$C_4$-alkoxy; particularly preferably fluorine, chlorine, bromine, methoxy or ethoxy; particularly preferably chlorine or methoxy;

$R^2$,$R^3$,$R^4$,$R^5$ are hydrogen;

$R^6$ is $C_1$–$C_4$-alkylsulfonyl; particularly preferably methylsulfonyl;

$R^7$ is hydroxyl, $C_1$–$C_6$-alkoxy, $C_1$–$C_4$-(alkylthio)carbonyloxy or phenylcarbonyloxy, where the phenyl radical may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl, $C_1$–$C_6$-alkoxy or phenylcarbonyloxy, where the phenyl radical may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

$R^8$,$R^9$ are $C_1$–$C_4$-alkyl;

$R^{10}$ is hydrogen or $C_1$–$C_4$-alkyl;

$R^{11}$ is hydrogen.

Very particular preference is given to the compounds of the formula Ia1 (≡I where $R^1$=Cl; $R^8$,$R^9$=$CH_3$; $R^{10}$,$R^{11}$=H), in particular to the compounds Ia1.1 to Ia1.300 of Table 1, where the radical definitions X and $R^1$ to $R^{11}$ are of particular importance for the compounds according to the invention, not only in combination with one another, but in each case also on their own.

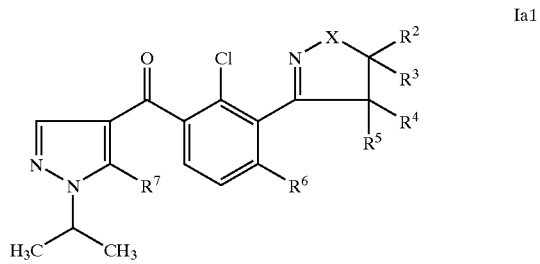

Ia1

TABLE 1

| No. | X | $R^2$ | $R^3$ | $R^4$ | $R^5$ | $R^6$ | $R^7$ |
|---|---|---|---|---|---|---|---|
| Ia1.1 | O | H | H | H | H | $SCH_3$ | OH |
| Ia1.2 | O | H | H | H | H | $SCH_2CH_3$ | OH |
| Ia1.3 | O | H | H | H | H | $SO_2CH_3$ | OH |
| Ia1.4 | O | H | H | H | H | $SO_2CH_2CH_3$ | OH |
| Ia1.5 | O | H | H | H | H | $SO_2CH(CH_3)_2$ | OH |
| Ia1.6 | O | H | H | H | H | $SO_2(CH_2)_2CH_3$ | OH |
| Ia1.7 | O | H | H | H | H | Cl | OH |
| Ia1.8 | O | H | H | H | H | Br | OH |
| Ia1.9 | O | H | H | H | H | $NO_2$ | OH |
| Ia1.10 | O | H | H | H | H | $CHF_2$ | OH |
| Ia1.11 | O | H | H | H | H | $CF_3$ | OH |
| Ia1.12 | O | H | H | H | H | $OCH_3$ | OH |
| Ia1.13 | O | H | H | H | H | $OCH_2CH_3$ | OH |
| Ia1.14 | O | H | H | H | H | $OCHF_2$ | OH |
| Ia1.15 | O | H | H | H | H | $OCF_3$ | OH |
| Ia1.16 | O | $CH_3$ | H | H | H | $SCH_3$ | OH |
| Ia1.17 | O | $CH_3$ | H | H | H | $SCH_2CH_3$ | OH |
| Ia1.18 | O | $CH_3$ | H | H | H | $SO_2CH_3$ | OH |
| Ia1.19 | O | $CH_3$ | H | H | H | $SO_2CH_2CH_3$ | OH |
| Ia1.20 | O | $CH_3$ | H | H | H | $SO_2CH(CH_3)_2$ | OH |
| Ia1.21 | O | $CH_3$ | H | H | H | $SO_2(CH_2)_2CH_3$ | OH |
| Ia1.22 | O | $CH_3$ | H | H | H | Cl | OH |
| Ia1.23 | O | $CH_3$ | H | H | H | Br | OH |
| Ia1.24 | O | $CH_3$ | H | H | H | $NO_2$ | OH |
| Ia1.25 | O | $CH_3$ | H | H | H | $CHF_2$ | OH |
| Ia1.26 | O | $CH_3$ | H | H | H | $CF_3$ | OH |
| Ia1.27 | O | $CH_3$ | H | H | H | $OCH_3$ | OH |
| Ia1.28 | O | $CH_3$ | H | H | H | $OCH_2CH_3$ | OH |
| Ia1.29 | O | $CH_3$ | H | H | H | $OCHF_2$ | OH |
| Ia1.30 | O | $CH_3$ | H | H | H | $OCF_3$ | OH |
| Ia1.31 | O | H | H | $CH_3$ | H | $SCH_3$ | OH |
| Ia1.32 | O | H | H | $CH_3$ | H | $SCH_2CH_3$ | OH |
| Ia1.33 | O | H | H | $CH_3$ | H | $SO_2CH_3$ | OH |
| Ia1.34 | O | H | H | $CH_3$ | H | $SO_2CH_2CH_3$ | OH |
| Ia1.35 | O | H | H | $CH_3$ | H | $SO_2CH(CH_3)_2$ | OH |
| Ia1.36 | O | H | H | $CH_3$ | H | $SO_2(CH_2)_2CH_3$ | OH |
| Ia1.37 | O | H | H | $CH_3$ | H | Cl | OH |
| Ia1.38 | O | H | H | $CH_3$ | H | Br | OH |
| Ia1.39 | O | H | H | $CH_3$ | H | $NO_2$ | OH |
| Ia1.40 | O | H | H | $CH_3$ | H | $CHF_2$ | OH |
| Ia1.41 | O | H | H | $CH_3$ | H | $CF_3$ | OH |
| Ia1.42 | O | H | H | $CH_3$ | H | $OCH_3$ | OH |
| Ia1.43 | O | H | H | $CH_3$ | H | $OCH_2CH_3$ | OH |
| Ia1.44 | O | H | H | $CH_3$ | H | $OCHF_2$ | OH |
| Ia1.45 | O | H | H | $CH_3$ | H | $OCF_3$ | OH |
| Ia1.46 | O | $CH_3$ | $CH_3$ | H | H | $SCH_3$ | OH |
| Ia1.47 | O | $CH_3$ | $CH_3$ | H | H | $SCH_2CH_3$ | OH |
| Ia1.48 | O | $CH_3$ | $CH_3$ | H | H | $SO_2CH_3$ | OH |
| Ia1.49 | O | $CH_3$ | $CH_3$ | H | H | $SO_2CH_2CH_3$ | OH |
| Ia1.50 | O | $CH_3$ | $CH_3$ | H | H | $SO_2CH(CH_3)_2$ | OH |
| Ia1.51 | O | $CH_3$ | $CH_3$ | H | H | $SO_2(CH_2)_2CH_3$ | OH |
| Ia1.52 | O | $CH_3$ | $CH_3$ | H | H | Cl | OH |
| Ia1.53 | O | $CH_3$ | $CH_3$ | H | H | Br | OH |
| Ia1.54 | O | $CH_3$ | $CH_3$ | H | H | $NO_2$ | OH |
| Ia1.55 | O | $CH_3$ | $CH_3$ | H | H | $CHF_2$ | OH |

TABLE 1-continued

| No. | X | R² | R³ | R⁴ | R⁵ | R⁶ | R⁷ |
|---|---|---|---|---|---|---|---|
| Ia1.56 | O | CH₃ | CH₃ | H | H | CF₃ | OH |
| Ia1.57 | O | CH₃ | CH₃ | H | H | OCH₃ | OH |
| Ia1.58 | O | CH₃ | CH₃ | H | H | OCH₂CH₃ | OH |
| Ia1.59 | O | CH₃ | CH₃ | H | H | OCHF₂ | OH |
| Ia1.60 | O | CH₃ | CH₃ | H | H | OCF₃ | OH |
| Ia1.61 | O | CH₃ | H | CH₃ | H | SCH₃ | OH |
| Ia1.62 | O | CH₃ | H | CH₃ | H | SCH₂CH₃ | OH |
| Ia1.63 | O | CH₃ | H | CH₃ | H | SO₂CH₃ | OH |
| Ia1.64 | O | CH₃ | H | CH₃ | H | SO₂CH₂CH₃ | OH |
| Ia1.65 | O | CH₃ | H | CH₃ | H | SO₂CH(CH₃)₂ | OH |
| Ia1.66 | O | CH₃ | H | CH₃ | H | SO₂(CH₂)₂CH₃ | OH |
| Ia1.67 | O | CH₃ | H | CH₃ | H | Cl | OH |
| Ia1.68 | O | CH₃ | H | CH₃ | H | Br | OH |
| Ia1.69 | O | CH₃ | H | CH₃ | H | NO₂ | OH |
| Ia1.70 | O | CH₃ | H | CH₃ | H | CHF₂ | OH |
| Ia1.71 | O | CH₃ | H | CH₃ | H | CF₃ | OH |
| Ia1.72 | O | CH₃ | H | CH₃ | H | OCH₃ | OH |
| Ia1.73 | O | CH₃ | H | CH₃ | H | OCH₂CH₃ | OH |
| Ia1.74 | O | CH₃ | H | CH₃ | H | OCHF₂ | OH |
| Ia1.75 | O | CH₃ | H | CH₃ | H | OCF₃ | OH |
| Ia1.76 | O | H | H | CH₃ | CH₃ | SCH₃ | OH |
| Ia1.77 | O | H | H | CH₃ | CH₃ | SCH₂CH₃ | OH |
| Ia1.78 | O | H | H | CH₃ | CH₃ | SO₂CH₃ | OH |
| Ia1.79 | O | H | H | CH₃ | CH₃ | SO₂CH₂CH₃ | OH |
| Ia1.80 | O | H | H | CH₃ | CH₃ | SO₂CH(CH₃)₂ | OH |
| Ia1.81 | O | H | H | CH₃ | CH₃ | SO₂(CH₂)₂CH₃ | OH |
| Ia1.82 | O | H | H | CH₃ | CH₃ | Cl | OH |
| Ia1.83 | O | H | H | CH₃ | CH₃ | Br | OH |
| Ia1.84 | O | H | H | CH₃ | CH₃ | NO₂ | OH |
| Ia1.85 | O | H | H | CH₃ | CH₃ | CHF₂ | OH |
| Ia1.86 | O | H | H | CH₃ | CH₃ | CF₃ | OH |
| Ia1.87 | O | H | H | CH₃ | CH₃ | OCH₃ | OH |
| Ia1.88 | O | H | H | CH₃ | CH₃ | OCH₂CH₃ | OH |
| Ia1.89 | O | H | H | CH₃ | CH₃ | OCHF₂ | OH |
| Ia1.90 | O | H | H | CH₃ | CH₃ | OCF₃ | OH |
| Ia1.91 | O | CH₃ | CH₃ | CH₃ | H | SCH₃ | OH |
| Ia1.92 | O | CH₃ | CH₃ | CH₃ | H | SCH₂CH₃ | OH |
| Ia1.93 | O | CH₃ | CH₃ | CH₃ | H | SO₂CH₃ | OH |
| Ia1.94 | O | CH₃ | CH₃ | CH₃ | H | SO₂CH₂CH₃ | OH |
| Ia1.95 | O | CH₃ | CH₃ | CH₃ | H | SO₂CH(CH₃)₂ | OH |
| Ia1.96 | O | CH₃ | CH₃ | CH₃ | H | SO₂(CH₂)₂CH₃ | OH |
| Ia1.97 | O | CH₃ | CH₃ | CH₃ | H | Cl | OH |
| Ia1.98 | O | CH₃ | CH₃ | CH₃ | H | Br | OH |
| Ia1.99 | O | CH₃ | CH₃ | CH₃ | H | NO₂ | OH |
| Ia1.100 | O | CH₃ | CH₃ | CH₃ | H | CHF₂ | OH |
| Ia1.101 | O | CH₃ | CH₃ | CH₃ | H | CF₃ | OH |
| Ia1.102 | O | CH₃ | CH₃ | CH₃ | H | OCH₃ | OH |
| Ia1.103 | O | CH₃ | CH₃ | CH₃ | H | OCH₂CH₃ | OH |
| Ia1.104 | O | CH₃ | CH₃ | CH₃ | H | OCHF₂ | OH |
| Ia1.105 | O | CH₃ | CH₃ | CH₃ | H | OCF₃ | OH |
| Ia1.106 | O | CH₃ | H | CH₃ | CH₃ | SCH₃ | OH |
| Ia1.107 | O | CH₃ | H | CH₃ | CH₃ | SCH₂CH₃ | OH |
| Ia1.108 | O | CH₃ | H | CH₃ | CH₃ | SO₂CH₃ | OH |
| Ia1.109 | O | CH₃ | H | CH₃ | CH₃ | SO₂CH₂CH₃ | OH |
| Ia1.110 | O | CH₃ | H | CH₃ | CH₃ | SO₂CH(CH₃)₂ | OH |
| Ia1.111 | O | CH₃ | H | CH₃ | CH₃ | SO₂(CH₂)₂CH₃ | OH |
| Ia1.112 | O | CH₃ | H | CH₃ | CH₃ | Cl | OH |
| Ia1.113 | O | CH₃ | H | CH₃ | CH₃ | Br | OH |
| Ia1.114 | O | CH₃ | H | CH₃ | CH₃ | NO₂ | OH |
| Ia1.115 | O | CH₃ | H | CH₃ | CH₃ | CHF₂ | OH |
| Ia1.116 | O | CH₃ | H | CH₃ | CH₃ | CF₃ | OH |
| Ia1.117 | O | CH₃ | H | CH₃ | CH₃ | OCH₃ | OH |
| Ia1.118 | O | CH₃ | H | CH₃ | CH₃ | OCH₂CH₃ | OH |
| Ia1.119 | O | CH₃ | H | CH₃ | CH₃ | OCHF₂ | OH |
| Ia1.120 | O | CH₃ | H | CH₃ | CH₃ | OCF₃ | OH |
| Ia1.121 | O | CH₃ | CH₃ | CH₃ | CH₃ | SCH₃ | OH |
| Ia1.122 | O | CH₃ | CH₃ | CH₃ | CH₃ | SCH₂CH₃ | OH |
| Ia1.123 | O | CH₃ | CH₃ | CH₃ | CH₃ | SO₂CH₃ | OH |
| Ia1.124 | O | CH₃ | CH₃ | CH₃ | CH₃ | SO₂CH₂CH₃ | OH |
| Ia1.125 | O | CH₃ | CH₃ | CH₃ | CH₃ | SO₂CH(CH₃)₂ | OH |
| Ia1.126 | O | CH₃ | CH₃ | CH₃ | CH₃ | SO₂(CH₂)₂CH₃ | OH |
| Ia1.127 | O | CH₃ | CH₃ | CH₃ | CH₃ | Cl | OH |
| Ia1.128 | O | CH₃ | CH₃ | CH₃ | CH₃ | Br | OH |
| Ia1.129 | O | CH₃ | CH₃ | CH₃ | CH₃ | NO₂ | OH |
| Ia1.130 | O | CH₃ | CH₃ | CH₃ | CH₃ | CHF₂ | OH |
| Ia1.131 | O | CH₃ | CH₃ | CH₃ | CH₃ | CF₃ | OH |
| Ia1.132 | O | CH₃ | CH₃ | CH₃ | CH₃ | OCH₃ | OH |
| Ia1.133 | O | CH₃ | CH₃ | CH₃ | CH₃ | OCH₂CH₃ | OH |
| Ia1.134 | O | CH₃ | CH₃ | CH₃ | CH₃ | OCHF₂ | OH |
| Ia1.135 | O | CH₃ | CH₃ | CH₃ | CH₃ | OCF₃ | OH |
| Ia1.136 | O | CH₂Cl | H | H | H | SCH₃ | OH |
| Ia1.137 | O | CH₂Cl | H | H | H | SCH₂CH₃ | OH |
| Ia1.138 | O | CH₂Cl | H | H | H | SO₂CH₃ | OH |
| Ia1.139 | O | CH₂Cl | H | H | H | SO₂CH₂CH₃ | OH |
| Ia1.140 | O | CH₂Cl | H | H | H | SO₂CH(CH₃)₂ | OH |
| Ia1.141 | O | CH₂Cl | H | H | H | SO₂(CH₂)₂CH₃ | OH |
| Ia1.142 | O | CH₂Cl | H | H | H | Cl | OH |
| Ia1.143 | O | CH₂Cl | H | H | H | Br | OH |
| Ia1.144 | O | CH₂Cl | H | H | H | NO₂ | OH |
| Ia1.145 | O | CH₂Cl | H | H | H | CHF₂ | OH |
| Ia1.146 | O | CH₂Cl | H | H | H | CF₃ | OH |
| Ia1.147 | O | CH₂Cl | H | H | H | OCH₃ | OH |
| Ia1.148 | O | CH₂Cl | H | H | H | OCH₂CH₃ | OH |
| Ia1.149 | O | CH₂Cl | H | H | H | OCHF₂ | OH |
| Ia1.150 | O | CH₂Cl | H | H | H | OCF₃ | OH |
| Ia1.151 | NCH₃ | H | H | H | H | SCH₃ | OH |
| Ia1.152 | NCH₃ | H | H | H | H | SCH₂CH₃ | OH |
| Ia1.153 | NCH₃ | H | H | H | H | SO₂CH₃ | OH |
| Ia1.154 | NCH₃ | H | H | H | H | SO₂CH₂CH₃ | OH |
| Ia1.155 | NCH₃ | H | H | H | H | SO₂CH(CH₃)₂ | OH |
| Ia1.156 | NCH₃ | H | H | H | H | SO₂(CH₂)₂CH₃ | OH |
| Ia1.157 | NCH₃ | H | H | H | H | Cl | OH |
| Ia1.158 | NCH₃ | H | H | H | H | Br | OH |
| Ia1.159 | NCH₃ | H | H | H | H | NO₂ | OH |
| Ia1.160 | NCH₃ | H | H | H | H | CHF₂ | OH |
| Ia1.161 | NCH₃ | H | H | H | H | CF₃ | OH |
| Ia1.162 | NCH₃ | H | H | H | H | OCH₃ | OH |
| Ia1.163 | NCH₃ | H | H | H | H | OCH₂CH₃ | OH |
| Ia1.164 | NCH₃ | H | H | H | H | OCHF₂ | OH |
| Ia1.165 | NCH₃ | H | H | H | H | OCF₃ | OH |
| Ia1.166 | NCH₃ | CH₃ | H | H | H | SCH₃ | OH |
| Ia1.167 | NCH₃ | CH₃ | H | H | H | SCH₂CH₃ | OH |
| Ia1.168 | NCH₃ | CH₃ | H | H | H | SO₂CH₃ | OH |
| Ia1.169 | NCH₃ | CH₃ | H | H | H | SO₂CH₂CH₃ | OH |
| Ia1.170 | NCH₃ | CH₃ | H | H | H | SO₂CH(CH₃)₂ | OH |
| Ia1.171 | NCH₃ | CH₃ | H | H | H | SO₂(CH₂)₂CH₃ | OH |
| Ia1.172 | NCH₃ | CH₃ | H | H | H | Cl | OH |
| Ia1.173 | NCH₃ | CH₃ | H | H | H | Br | OH |
| Ia1.174 | NCH₃ | CH₃ | H | H | H | NO₂ | OH |
| Ia1.175 | NCH₃ | CH₃ | H | H | H | CHF₂ | OH |
| Ia1.176 | NCH₃ | CH₃ | H | H | H | CF₃ | OH |
| Ia1.177 | NCH₃ | CH₃ | H | H | H | OCH₃ | OH |
| Ia1.178 | NCH₃ | CH₃ | H | H | H | OCH₂CH₃ | OH |
| Ia1.179 | NCH₃ | CH₃ | H | H | H | OCHF₂ | OH |
| Ia1.180 | NCH₃ | CH₃ | H | H | H | OCF₃ | OH |
| Ia1.181 | NCH₃ | H | H | CH₃ | H | SCH₃ | OH |
| Ia1.182 | NCH₃ | H | H | CH₃ | H | SCH₂CH₃ | OH |
| Ia1.183 | NCH₃ | H | H | CH₃ | H | SO₂CH₃ | OH |
| Ia1.184 | NCH₃ | H | H | CH₃ | H | SO₂CH₂CH₃ | OH |
| Ia1.185 | NCH₃ | H | H | CH₃ | H | SO₂CH(CH₃)₂ | OH |
| Ia1.186 | NCH₃ | H | H | CH₃ | H | SO₂(CH₂)₂CH₃ | OH |
| Ia1.187 | NCH₃ | H | H | CH₃ | H | Cl | OH |
| Ia1.188 | NCH₃ | H | H | CH₃ | H | Br | OH |
| Ia1.189 | NCH₃ | H | H | CH₃ | H | NO₂ | OH |
| Ia1.190 | NCH₃ | H | H | CH₃ | H | CHF₂ | OH |
| Ia1.191 | NCH₃ | H | H | CH₃ | H | CF₃ | OH |
| Ia1.192 | NCH₃ | H | H | CH₃ | H | OCH₃ | OH |
| Ia1.193 | NCH₃ | H | H | CH₃ | H | OCH₂CH₃ | OH |
| Ia1.194 | NCH₃ | H | H | CH₃ | H | OCHF₂ | OH |
| Ia1.195 | NCH₃ | H | H | CH₃ | H | OCF₃ | OH |
| Ia1.196 | NCH₃ | CH₃ | CH₃ | H | H | SCH₃ | OH |
| Ia1.197 | NCH₃ | CH₃ | CH₃ | H | H | SCH₂CH₃ | OH |
| Ia1.198 | NCH₃ | CH₃ | CH₃ | H | H | SO₂CH₃ | OH |
| Ia1.199 | NCH₃ | CH₃ | CH₃ | H | H | SO₂CH₂CH₃ | OH |
| Ia1.200 | NCH₃ | CH₃ | CH₃ | H | H | SO₂CH(CH₃)₂ | OH |
| Ia1.201 | NCH₃ | CH₃ | CH₃ | H | H | SO₂(CH₂)₂CH₃ | OH |
| Ia1.202 | NCH₃ | CH₃ | CH₃ | H | H | Cl | OH |
| Ia1.203 | NCH₃ | CH₃ | CH₃ | H | H | Br | OH |
| Ia1.204 | NCH₃ | CH₃ | CH₃ | H | H | NO₂ | OH |
| Ia1.205 | NCH₃ | CH₃ | CH₃ | H | H | CHF₂ | OH |
| Ia1.206 | NCH₃ | CH₃ | CH₃ | H | H | CF₃ | OH |
| Ia1.207 | NCH₃ | CH₃ | CH₃ | H | H | OCH₃ | OH |
| Ia1.208 | NCH₃ | CH₃ | CH₃ | H | H | OCH₂CH₃ | OH |
| Ia1.209 | NCH₃ | CH₃ | CH₃ | H | H | OCHF₂ | OH |

TABLE 1-continued

| No. | X | R² | R³ | R⁴ | R⁵ | R⁶ | R⁷ |
|---|---|---|---|---|---|---|---|
| Ia1.210 | NCH₃ | CH₃ | CH₃ | H | H | OCF₃ | OH |
| Ia1.211 | NCH₃ | CH₃ | H | CH₃ | H | SCH₃ | OH |
| Ia1.212 | NCH₃ | CH₃ | H | CH₃ | H | SCH₂CH₃ | OH |
| Ia1.213 | NCH₃ | CH₃ | H | CH₃ | H | SO₂CH₃ | OH |
| Ia1.214 | NCH₃ | CH₃ | H | CH₃ | H | SO₂CH₂CH₃ | OH |
| Ia1.215 | NCH₃ | CH₃ | H | CH₃ | H | SO₂CH(CH₃)₂ | OH |
| Ia1.216 | NCH₃ | CH₃ | H | CH₃ | H | SO₂(CH₂)₂CH₃ | OH |
| Ia1.217 | NCH₃ | CH₃ | H | CH₃ | H | Cl | OH |
| Ia1.218 | NCH₃ | CH₃ | H | CH₃ | H | Br | OH |
| Ia1.219 | NCH₃ | CH₃ | H | CH₃ | H | NO₂ | OH |
| Ia1.220 | NCH₃ | CH₃ | H | CH₃ | H | CHF₂ | OH |
| Ia1.221 | NCH₃ | CH₃ | H | CH₃ | H | CF₃ | OH |
| Ia1.222 | NCH₃ | CH₃ | H | CH₃ | H | OCH₃ | OH |
| Ia1.223 | NCH₃ | CH₃ | H | CH₃ | H | OCH₂CH₃ | OH |
| Ia1.224 | NCH₃ | CH₃ | H | CH₃ | H | OCHF₂ | OH |
| Ia1.225 | NCH₃ | CH₃ | H | CH₃ | H | OCF₃ | OH |
| Ia1.226 | NCH₃ | H | H | CH₃ | CH₃ | SCH₃ | OH |
| Ia1.227 | NCH₃ | H | H | CH₃ | CH₃ | SCH₂CH₃ | OH |
| Ia1.228 | NCH₃ | H | H | CH₃ | CH₃ | SO₂CH₃ | OH |
| Ia1.229 | NCH₃ | H | H | CH₃ | CH₃ | SO₂CH₂CH₃ | OH |
| Ia1.230 | NCH₃ | H | H | CH₃ | CH₃ | SO₂CH(CH₃)₂ | OH |
| Ia1.231 | NCH₃ | H | H | CH₃ | CH₃ | SO₂(CH₂)₂CH₃ | OH |
| Ia1.232 | NCH₃ | H | H | CH₃ | CH₃ | Cl | OH |
| Ia1.233 | NCH₃ | H | H | CH₃ | CH₃ | Br | OH |
| Ia1.234 | NCH₃ | H | H | CH₃ | CH₃ | NO₂ | OH |
| Ia1.235 | NCH₃ | H | H | CH₃ | CH₃ | CHF₂ | OH |
| Ia1.236 | NCH₃ | H | H | CH₃ | CH₃ | CF₃ | OH |
| Ia1.237 | NCH₃ | H | H | CH₃ | CH₃ | OCH₃ | OH |
| Ia1.238 | NCH₃ | H | H | CH₃ | CH₃ | OCH₂CH₃ | OH |
| Ia1.239 | NCH₃ | H | H | CH₃ | CH₃ | OCHF₂ | OH |
| Ia1.240 | NCH₃ | H | H | CH₃ | CH₃ | OCF₃ | OH |
| Ia1.241 | NCH₃ | CH₃ | CH₃ | CH₃ | H | SCH₃ | OH |
| Ia1.242 | NCH₃ | CH₃ | CH₃ | CH₃ | H | SCH₂CH₃ | OH |
| Ia1.243 | NCH₃ | CH₃ | CH₃ | CH₃ | H | SO₂CH₃ | OH |
| Ia1.244 | NCH₃ | CH₃ | CH₃ | CH₃ | H | SO₂CH₂CH₃ | OH |
| Ia1.245 | NCH₃ | CH₃ | CH₃ | CH₃ | H | SO₂CH(CH₃)₂ | OH |
| Ia1.246 | NCH₃ | CH₃ | CH₃ | CH₃ | H | SO₂(CH₂)₂CH₃ | OH |
| Ia1.247 | NCH₃ | CH₃ | CH₃ | CH₃ | H | Cl | OH |
| Ia1.248 | NCH₃ | CH₃ | CH₃ | CH₃ | H | Br | OH |
| Ia1.249 | NCH₃ | CH₃ | CH₃ | CH₃ | H | NO₂ | OH |
| Ia1.250 | NCH₃ | CH₃ | CH₃ | CH₃ | H | CHF₂ | OH |
| Ia1.251 | NCH₃ | CH₃ | CH₃ | CH₃ | H | CF₃ | OH |
| Ia1.252 | NCH₃ | CH₃ | CH₃ | CH₃ | H | OCH₃ | OH |
| Ia1.253 | NCH₃ | CH₃ | CH₃ | CH₃ | H | OCH₂CH₃ | OH |
| Ia1.254 | NCH₃ | CH₃ | CH₃ | CH₃ | H | OCHF₂ | OH |
| Ia1.255 | NCH₃ | CH₃ | CH₃ | CH₃ | H | OCF₃ | OH |
| Ia1.256 | NCH₃ | CH₃ | H | CH₃ | CH₃ | SCH₃ | OH |
| Ia1.257 | NCH₃ | CH₃ | H | CH₃ | CH₃ | SCH₂CH₃ | OH |
| Ia1.258 | NCH₃ | CH₃ | H | CH₃ | CH₃ | SO₂CH₃ | OH |
| Ia1.259 | NCH₃ | CH₃ | H | CH₃ | CH₃ | SO₂CH₂CH₃ | OH |
| Ia1.260 | NCH₃ | CH₃ | H | CH₃ | CH₃ | SO₂CH(CH₃)₂ | OH |
| Ia1.261 | NCH₃ | CH₃ | H | CH₃ | CH₃ | SO₂(CH₂)₂CH₃ | OH |
| Ia1.262 | NCH₃ | CH₃ | H | CH₃ | CH₃ | Cl | OH |
| Ia1.263 | NCH₃ | CH₃ | H | CH₃ | CH₃ | Br | OH |
| Ia1.264 | NCH₃ | CH₃ | H | CH₃ | CH₃ | NO₂ | OH |
| Ia1.265 | NCH₃ | CH₃ | H | CH₃ | CH₃ | CHF₂ | OH |
| Ia1.266 | NCH₃ | CH₃ | H | CH₃ | CH₃ | CF₃ | OH |
| Ia1.267 | NCH₃ | CH₃ | H | CH₃ | CH₃ | OCH₃ | OH |
| Ia1.268 | NCH₃ | CH₃ | H | CH₃ | CH₃ | OCH₂CH₃ | OH |
| Ia1.269 | NCH₃ | CH₃ | H | CH₃ | CH₃ | OCHF₂ | OH |
| Ia1.270 | NCH₃ | CH₃ | H | CH₃ | CH₃ | OCF₃ | OH |
| Ia1.271 | NCH₃ | CH₃ | CH₃ | CH₃ | CH₃ | SCH₃ | OH |
| Ia1.272 | NCH₃ | CH₃ | CH₃ | CH₃ | CH₃ | SCH₂CH₃ | OH |
| Ia1.273 | NCH₃ | CH₃ | CH₃ | CH₃ | CH₃ | SO₂CH₃ | OH |
| Ia1.274 | NCH₃ | CH₃ | CH₃ | CH₃ | CH₃ | SO₂CH₂CH₃ | OH |
| Ia1.275 | NCH₃ | CH₃ | CH₃ | CH₃ | CH₃ | SO₂CH(CH₃)₂ | OH |
| Ia1.276 | NCH₃ | CH₃ | CH₃ | CH₃ | CH₃ | SO₂(CH₂)₂CH₃ | OH |
| Ia1.277 | NCH₃ | CH₃ | CH₃ | CH₃ | CH₃ | Cl | OH |
| Ia1.278 | NCH₃ | CH₃ | CH₃ | CH₃ | CH₃ | Br | OH |
| Ia1.279 | NCH₃ | CH₃ | CH₃ | CH₃ | CH₃ | NO₂ | OH |
| Ia1.280 | NCH₃ | CH₃ | CH₃ | CH₃ | CH₃ | CHF₂ | OH |
| Ia1.281 | NCH₃ | CH₃ | CH₃ | CH₃ | CH₃ | CF₃ | OH |
| Ia1.282 | NCH₃ | CH₃ | CH₃ | CH₃ | CH₃ | OCH₃ | OH |
| Ia1.283 | NCH₃ | CH₃ | CH₃ | CH₃ | CH₃ | OCH₂CH₃ | OH |
| Ia1.284 | NCH₃ | CH₃ | CH₃ | CH₃ | CH₃ | OCHF₂ | OH |
| Ia1.285 | NCH₃ | CH₃ | CH₃ | CH₃ | CH₃ | OCF₃ | OH |
| Ia1.286 | NCH₃ | CH₂Cl | H | H | H | SCH₃ | OH |
| Ia1.287 | NCH₃ | CH₂Cl | H | H | H | SCH₂CH₃ | OH |
| Ia1.288 | NCH₃ | CH₂Cl | H | H | H | SO₂CH₃ | OH |
| Ia1.289 | NCH₃ | CH₂Cl | H | H | H | SO₂CH₂CH₃ | OH |
| Ia1.290 | NCH₃ | CH₂Cl | H | H | H | SO₂CH(CH₃)₂ | OH |
| Ia1.291 | NCH₃ | CH₂Cl | H | H | H | SO₂(CH₂)₂CH₃ | OH |
| Ia1.292 | NCH₃ | CH₂Cl | H | H | H | Cl | OH |
| Ia1.293 | NCH₃ | CH₂Cl | H | H | H | Br | OH |
| Ia1.294 | NCH₃ | CH₂Cl | H | H | H | NO₂ | OH |
| Ia1.295 | NCH₃ | CH₂Cl | H | H | H | CHF₂ | OH |
| Ia1.296 | NCH₃ | CH₂Cl | H | H | H | CF₃ | OH |
| Ia1.297 | NCH₃ | CH₂Cl | H | H | H | OCH₃ | OH |
| Ia1.298 | NCH₃ | CH₂Cl | H | H | H | OCH₂CH₃ | OH |
| Ia1.299 | NCH₃ | CH₂Cl | H | H | H | OCHF₂ | OH |
| Ia1.300 | NCH₃ | CH₂Cl | H | H | H | OCF₃ | OH |

Extraordinary preference is also given to the compounds of the formula Ia2, in particular to the compounds Ia2.1 to Ia2.300, which differ from the corresponding compounds Ia1.1 to Ia1.300 in that $R^{11}$ is methyl.

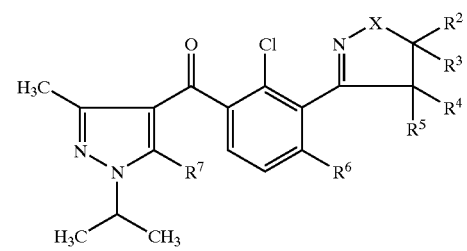

Ia2

Extraordinary preference is also given to the compounds of the formula Ia3, in particular to the compounds Ia3.1 to Ia3.300, which differ from the compounds Ia1.1 to Ia1.300 in that $R^8$ is ethyl.

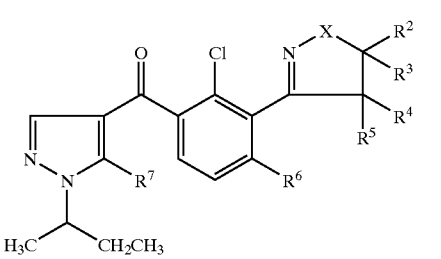

Ia3

Extraordinary preference is also given to the compounds of the formula Ia4, in particular to the compounds Ia4.1 to Ia4.300, which differ from the compounds Ia1.1 to Ia1.300 in that $R^8$ is ethyl and $R^{11}$ is methyl.

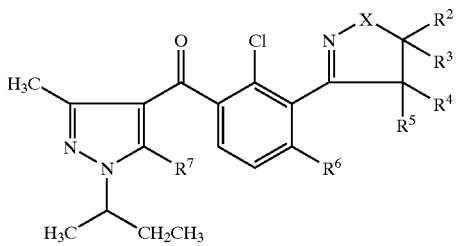

Ia4

Extraordinary preference is also given to the compounds of the formula Ia5, in particular to the compounds Ia5.1 to Ia5.300, which differ from the compounds Ia1.1 to Ia1.300 in that $R^8$ is 1-methyl-1-ethyl.

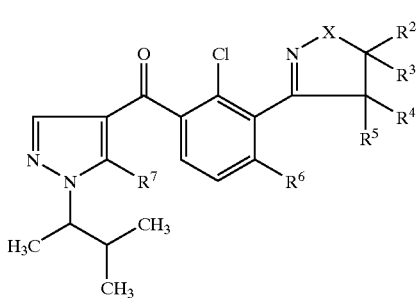

Ia5

Extraordinary preference is also given to the compounds of the formula Ia6, in particular to the compounds Ia6.1 to Ia6.300, which differ from the compounds Ia1.1 to Ia1.300 in that $R^8$ is 1-methyl-1-ethyl and $R^{11}$ is methyl.

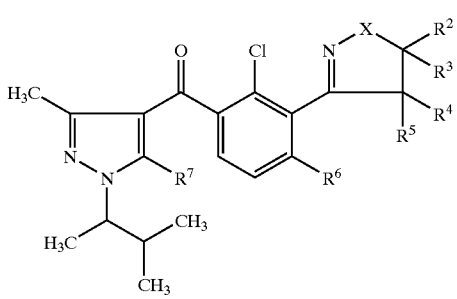

Ia6

Extraordinary preference is also given to the compounds of the formula Ia7, in particular to the compounds Ia7.1 to Ia7.300, which differ from the compounds Ia1.1 to Ia1.300 in that $R^{10}$ is methyl.

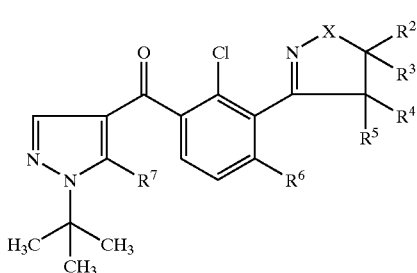

Ia7

Extraordinary preference is also given to the compounds of the formula Ia8, in particular to the compounds Ia8.1 to Ia8.300, which differ from the compounds Ia1.1 to Ia1.300 in that $R^{10}$ is methyl and $R^{11}$ is methyl.

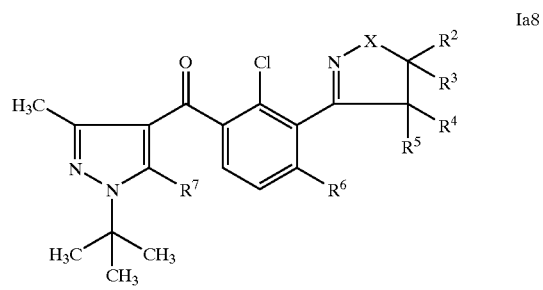

Ia8

Extraordinary preference is also given to the compounds of the formula Ia9, in particular to the compounds Ia9.1 to Ia9.300, which differ from the compounds Ia1.1 to Ia1.300 in that $R^8$ and $R^9$ are 1-methyl-1-ethyl.

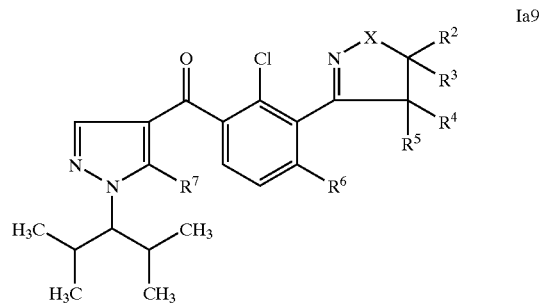

Ia9

Extraordinary preference is also given to the compounds of the formula Ia10, in particular to the compounds Ia10.1 to Ia10.300, which differ from the compounds Ia1.1 to Ia1.300 in that $R^8$ and $R^9$ are 1-methyl-1-ethyl and $R^{11}$ is methyl.

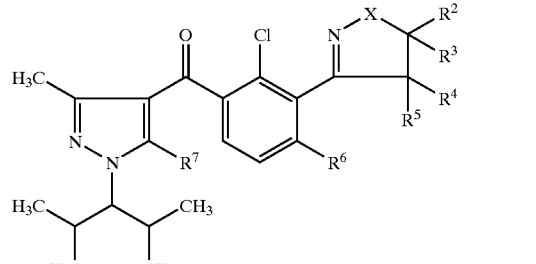

Ia10

Extraordinary preference is also given to the compounds of the formula Ia11, in particular to the compounds Ia11.1 to Ia11.300, which differ from the compounds Ia1.1 to Ia1.300 in that $R^8$ is ethyl and $R^{10}$ is methyl.

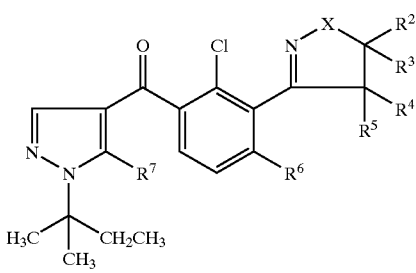
Ia11

Extraordinary preference is also given to the compounds of the formula Ia12, in particular to the compounds Ia12.1 to Ia12.300, which differ from the corresponding compounds Ia1.1 to Ia1.300 in that $R^8$ is ethyl and $R^{10}$ and $R^{11}$ are methyl.

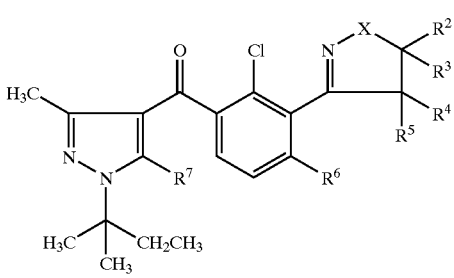
Ia12

Extraordinary preference is also given to the compounds of the formula Ia13, in particular to the compounds Ia13.1 to Ia13.300, which differ from the compounds Ia1.1 to Ia1.300 in that $R^1$ is methoxy.

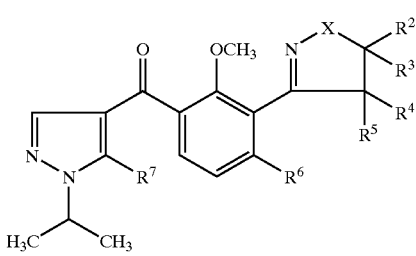
Ia13

Extraordinary preference is also given to the compounds of the formula Ia14, in particular to the compounds Ia14.1 to Ia14.300, which differ from the corresponding compounds Ia1.1 to Ia1.300 in that $R^1$ is methoxy and $R^{11}$ is methyl.

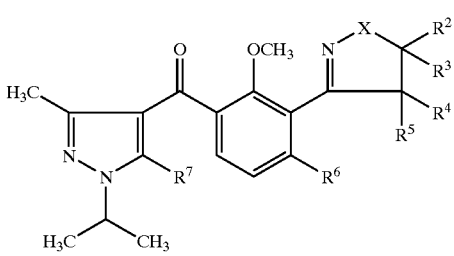
Ia14

Extraordinary preference is also given to the compounds of the formula Ia15, in particular to the compounds Ia15.1 to Ia15.300, which differ from the compounds Ia1.1 to Ia1.300 in that $R^1$ is methoxy and $R^8$ is ethyl.

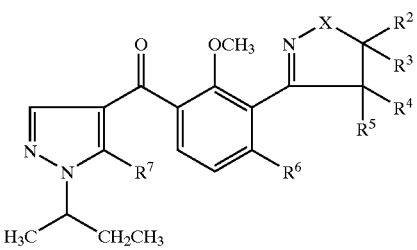
Ia15

Extraordinary preference is also given to the compounds of the formula Ia16, in particular to the compounds Ia16.1 to Ia16.300, which differ from the compounds Ia1.1 to Ia1.300 in $R^1$ is methoxy, $R^8$ is ethyl and $R^{11}$ is methyl.

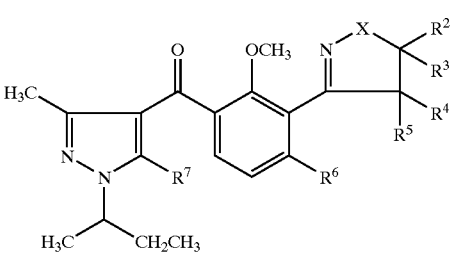
Ia16

Extraordinary preference is also given to the compounds of the formula Ia17, in particular to the compounds Ia17.1 to Ia17.300, which differ from the compounds Ia1.1 to Ia1.300 in that $R^1$ is methoxy and $R^8$ is 1-methyl-1-ethyl.

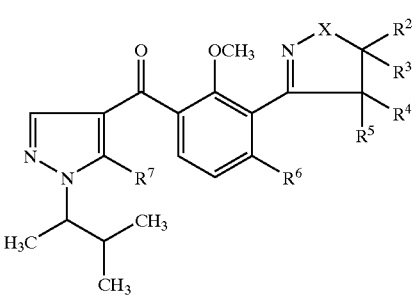
Ia17

Extraordinary preference is also given to the compounds of the formula Ia18, in particular to the compounds Ia18.1 to Ia18.300, which differ from the compounds Ia1.1 to Ia1.300 in that $R^1$ is methoxy, $R^8$ is 1-methyl-1-ethyl and $R^{11}$ is methyl.

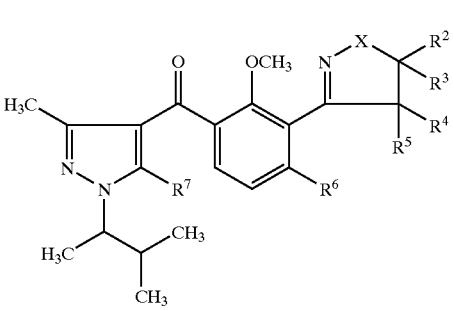
Ia18

Extraordinary preference is also given to the compounds of the formula Ia19, in particular to the compounds Ia19.1 to Ia19.300, which differ from the compounds Ia1.1 to Ia1.300 in that $R^1$ is methoxy and $R^{10}$ is methyl.

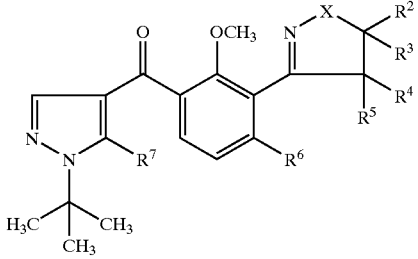

Ia19

Extraordinary preference is also given to the compounds of the formula Ia20, in particular to the compounds Ia20.1 to Ia20.300, which differ from the compounds Ia1.1 to Ia1.300 in that $R^1$ is methoxy, $R^{10}$ is methyl and $R^{11}$ is methyl.

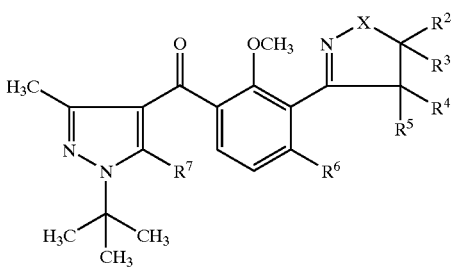

Ia20

Extraordinary preference is also given to the compounds of the formula Ia21, in particular to the compounds Ia21.1 to Ia21.300, which differ from the compounds Ia1.1 to Ia1.300 in that $R^1$ is methoxy and $R^8$ and $R^9$ are 1-methyl-1-ethyl.

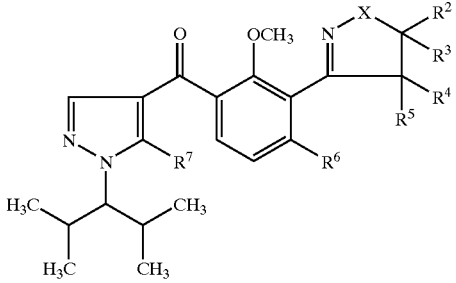

Ia21

Extraordinary preference is also given to the compounds of the formula Ia22, in particular to the compounds Ia22.1 to Ia22.300, which differ from the compounds Ia1.1 to Ia1.300 in that $R^1$ is methoxy, $R^8$ and $R^9$ are 1-methyl-1-ethyl and $R^{11}$ is methyl.

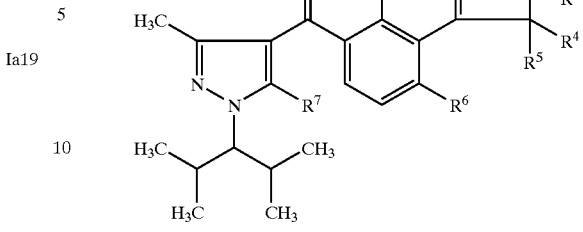

Ia22

Extraordinary preference is also given to the compounds of the formula Ia23, in particular to the compounds Ia23.1 to Ia23.300, which differ from the compounds Ia1.1 to Ia1.300 in that $R^1$ is methoxy, $R^8$ is ethyl and $R^{10}$ is methyl.

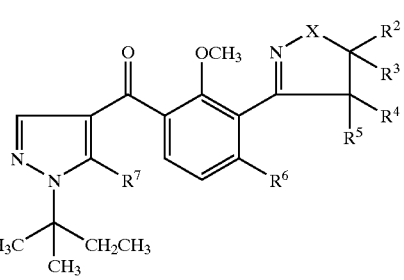

Ia23

Extraordinary preference is also given to the compounds of the formula Ia24, in particular to the compounds Ia24.1 to Ia24.300, which differ from the compounds Ia1.1 to Ia1.300 in that $R^1$ is methoxy, $R^8$ is ethyl and $R^{10}$ and $R^{11}$ are methyl.

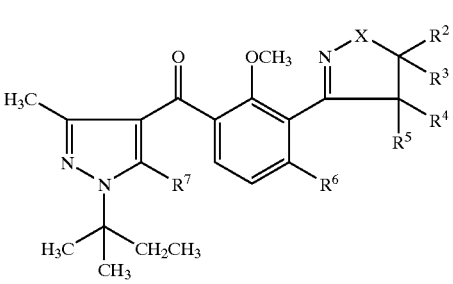

Ia24

The 3-(heterocyclyl)benzoylpyrazole derivatives of the formula I can be obtained by various routes, for example by the processes below.

Process A:

Reaction of pyrazoles of the formula II with an activated benzoic acid IIIα or a benzoic acid IIIβ, which is preferably activated in situ, to give the corresponding acylation product IV, followed by rearrangement, gives compounds of the formula I where $R^7$=OH.

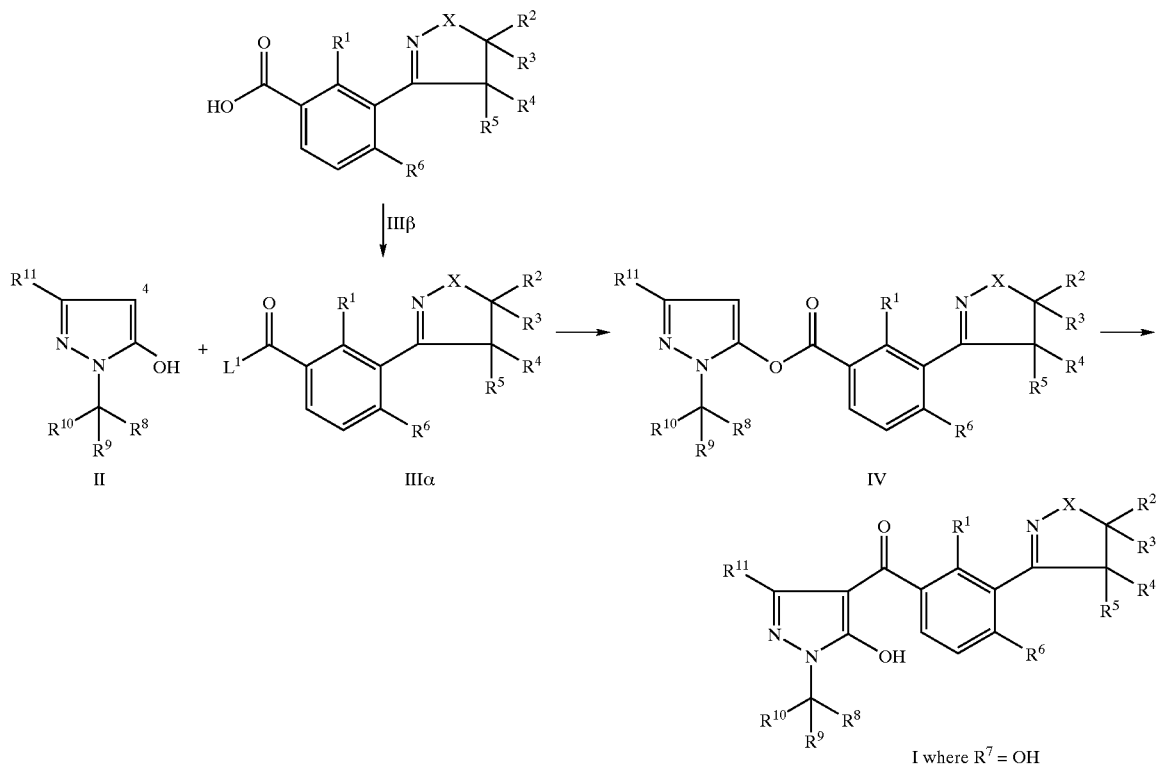

$L^1$ is a nucleophilically displaceable leaving group, such as halogen, for example bromine, chlorine, hetaryl, for example imidazolyl, pyridyl, carboxylate, for example acetate, trifluoroacetate etc.

The activated benzoic acid can be employed directly, such as in the case of the benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

It may be advantageous to carry out the acylation reaction in the presence of a base. The reactants and the auxiliary base are advantageously employed in equimolar amounts here. A slight excess of auxiliary base, for example from 1.2 to 1.5 molar equivalents, based on II, may be advantageous in certain cases.

Suitable auxiliary bases are tertiary alkylamines, pyridine or alkali metal carbonates. Suitable for use as solvents are, for example, chlorinated hydrocarbons, such as methylene chloride, 1,2-dichloroethane, aromatic hydrocarbons, such as toluene, xylene, chlorobenzene, ethers, such as diethyl ether, methyl tert-butyl ether, dimethoxyethane, tetrahydrofuran, dioxane, polar aprotic solvents, such as acetonitrile, dimethylformamide, dimethyl sulfoxide, or esters, such as ethyl acetate, or mixtures of these.

If the activated carboxylic acid components used are benzoyl halides, it may be advantageous to cool the reaction mixture to 0–10° C. when adding this reaction partner. The mixture is subsequently stirred at 20–100° C., preferably at 25–50° C., until the reaction has ended. Work-up is carried out in a customary manner, for example by pouring the reaction mixture into water and extracting the product of value. Solvents which are particularly suitable for this purpose are methylene chloride, diethyl ether, dimethoxyethane and ethyl acetate. The organic phase is dried and the solvent is removed, after which the crude ester can be employed for the rearrangement without any further purification.

The rearrangement of the esters to give the compounds of the formula I is advantageously carried out at 20–400° C. in a solvent and in the presence of a base and, if appropriate, using a cyano compound as catalyst.

Suitable solvents are, for example, acetonitrile, methylene chloride, 1,2-dichloroethane, dioxane, ethyl acetate, dimethoxyethane, toluene or mixtures of these. Preferred solvents are acetonitrile and dioxane.

Suitable bases are tertiary amines, such as triethylamine or pyridine, or alkali metal carbonates, such as sodium carbonate or potassium carbonate, which are preferably employed in an equimolar amount or an up to four-fold excess, based on the ester. Preference is given to using triethylamine or alkali metal carbonates, preferably in twice the equimolar amount, based on the ester.

Suitable cyano compounds are inorganic cyanides, such as sodium cyanide and potassium cyanide, and organic cyano compounds, such as acetone cyanohydrin and trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, and the mixture is dried and concentrated. (Examples of the preparation of esters of hydroxypyrazoles and for the rearrangement of the esters are given, for example, in EP-A 282 944 and U.S. Pat. No. 4,643,757).

However, it is also possible to generate the "acylation product" IV in situ by reacting a pyrazole of the formula II, or an alkali metal salt thereof, with a 3-(heterocyclyl) benzene derivative of the formula V in the presence of carbon monoxide, a catalyst and a base.

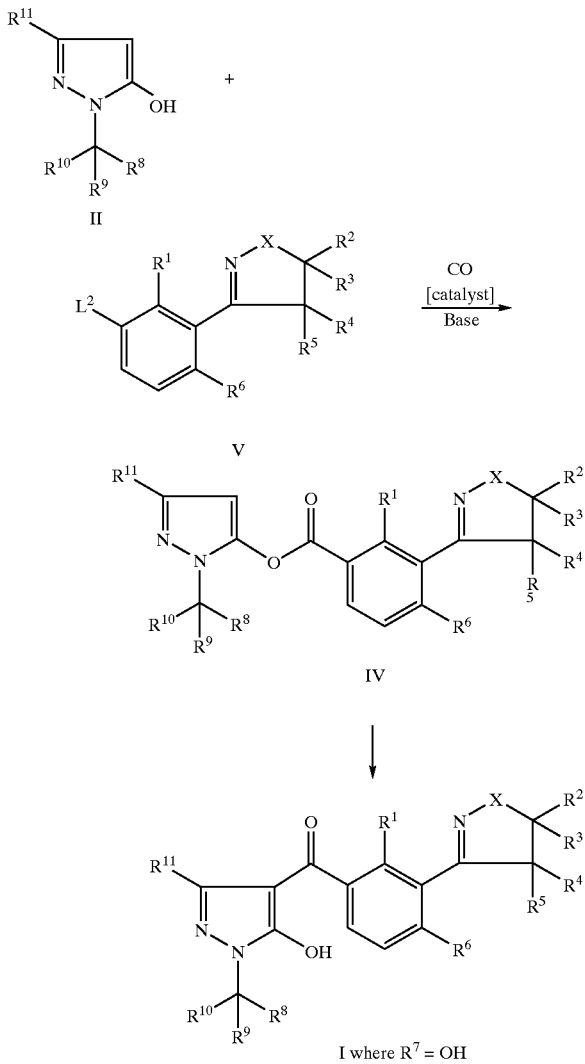

$L^2$ is a leaving group, such as halogen, for example chlorine, bromine or iodine, or sulfonate, such as mesylate or triflate; preference is given to bromine or triflate.

The "acylation product" IV proceeds to react, directly or indirectly, to give the 3-(heterocyclyl)benzoylpyrazole derivative of the formula I.

Suitable catalysts are palladium-ligand complexes in which the palladium is present in oxidation state 0, metallic palladium, which has optionally been absorbed on a carrier, and preferably palladium(II) salts. The reaction with palladium(II) salts and metallic palladium is preferably carried out in the presence of complex ligands.

An example of a suitable palladium(0)-ligand complex is tetrakis(triphenylphosphine)palladium.

Metallic palladium is preferably absorbed on an inert carrier such as, for example, activated carbon, silica, alumina, barium sulfate or calcium carbonate. The reaction is preferably carried out in the presence of complex ligands such as, for example, triphenylphosphine.

Examples of suitable palladium(II) salts are palladium acetate and palladium chloride. The presence of complex ligands such as, for example, triphenylphosphine is preferred.

Suitable complex ligands for the palladium-ligand complexes, or in whose presence the reaction is preferably carried out with metallic palladium or palladium(II) salts, are tertiary phosphines whose structure is represented by the following formulae:

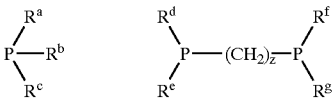

where z is 1 to 4 and the radicals $R^a$ to $R^g$ are $C_1$–$C_6$-alkyl, $C_3$–$C_6$-cycloalkyl, aryl-$C_1$–$C_2$-alkyl or, preferably, aryl. Aryl is, for example, naphthyl and unsubstituted or substituted phenyl such as, for example, 2-tolyl and, in particular, unsubstituted phenyl.

The complex palladium salts can be prepared in a manner known per se starting from commercially available palladium salts such as palladium chloride or palladium acetate and the appropriate phosphines such as, for example, triphenylphosphine or 1,2-bis(diphenylphosphino)ethane. Many of the complexed palladium salts are commercially available. Preferred palladium salts are [(R)(+)2,2'-bis (diphenylphosphino)-1,1'-binaphthyl]palladium(II) chloride, bis(triphenylphosphine)palladium(II) acetate and, in particular, bis(triphenylphosphine)palladium(II) chloride.

The palladium catalyst is usually employed in a concentration of from 0.05 to 5 mol %, and preferably 1–3 mol %.

Suitable bases are tertiary amines, such as, for example, N-methylpiperidine, ethyldiisopropylamine, 1,8-bisdimethylaminonaphthalene or, in particular, triethylamine. Also suitable are alkali metal carbonates, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on the 3-(heterocylyl)benzene derivative of the formula V.

Suitable solvents are nitriles, such as benzonitrile and acetonitrile, amides, such as dimethylformamide, dimethylacetamide, tetra-$C_1$–$C_4$-alkylureas or N-methylpyrrolidone and, preferably, ethers, such as tetrahydrofuran and methyl tert-butyl ethers. Particular preference is given to ethers, such as 1,4-dioxane and dimethoxyethane.

Process B:

Compounds of the formula I where $R^7 \neq$ hydroxyl are obtained by reacting compounds of the formula I where $R^7$=hydroxyl with alkylating agents, sulfonylating agents or acylating agents $L^3$—$R^{7a}$ (VI).

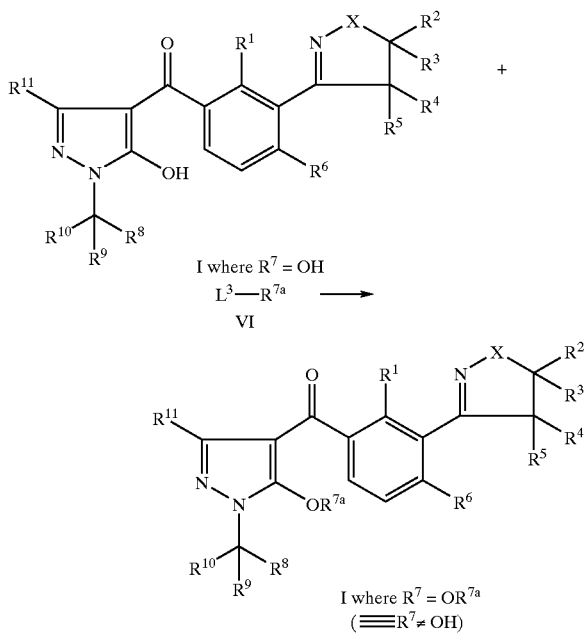

I where $R^7$ = OH
$L^3$—$R^{7a}$
VI

→

I where $R^7$ = $OR^{7a}$
($\equiv R^7 \neq$ OH)

$L^3$ is a nucleophilically displaceable leaving group, such as halogen, for example bromine or chlorine, acyloxy, for example acetyloxy, ethylcarbonyloxy, or alkylsulfonyloxy, for example methylsulfonyloxy or trifluoromethylsulfonyloxy.

$R^{7a}$ is $C_1$–$C_6$-alkyl, $C_3$–$C_6$-alkenyl, $C_1$–$C_6$-alkylsulfonyl, $C_1$–$C_6$-alkylcarbonyl, $C_1$–$C_6$-(alkylthio)carbonyl, phenylsulfonyl or phenylcarbonyl, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

The compounds of the formula VI can be employed directly, such as, for example, in the case of the sulfonyl halides or sulfonic anhydrides, or be generated in situ, for example activated sulfonic acids (using sulfonic acid and dicyclohexylcarbonyldiimide, carbonyldiimidazole, etc.).

The starting materials are generally employed in equimolar amounts. However, it may also be advantageous to employ an excess of one component or the other.

If appropriate, it may be advantageous to carry out the reaction in the presence of a base. The reactants and the auxiliary base are advantageously employed in equimolar amounts here. An excess of auxiliary base, for example from 1.5 to 3 molar equivalents, based on I, may be advantageous in certain cases.

Suitable auxiliary bases are tertiary alkylamines, such as triethylamine, pyridine, alkali metal carbonates, for example sodium carbonate or potassium carbonate, and alkali metal hydrides, for example sodium hydride. Preference is given to using triethylamine and pyridine.

Suitable solvents are, for example, chlorinated hydrocarbons, such as methylene chloride and 1,2-dichloroethane, aromatic hydrocarbons, for example toluene, xylene, chlorobenzene, ethers, such as diethyl ether, methyl tert-butyl ether, tetrahydrofuran and dioxane, polar aprotic solvents, such as acetonitrile, dimethylformamide, dimethyl sulfoxide, or esters, such as ethyl acetate, or mixtures of these.

In general, the reaction temperature is in the range from 0° C. to the boiling point of the reaction mixture.

Work-up can be carried out in a manner known per se to give the product.

The pyrazoles of the formula II used as starting materials are known or can be prepared by processes known per se (for example EP-A 240 001 and J. Prakt. Chem. 315, 383 (1973)).

The activated benzoic acids IIIα can be obtained in a manner known per se from the benzoic acids IIIβ. The latter for their part are obtained by hydrolysis from the corresponding esters VII. These can be prepared by converting an oxime or hydrazone of the formula VIII into the corresponding hydroxyamic acid halide, in particular hydroxamic acid chloride, or carbohydrazide halide, in particular carbohydrazide chloride; generating a nitrile oxide or nitrileimine in situ and reacting this with an alkene (cf. for example Chem. Ber. 106, 3258–3274 (1973).

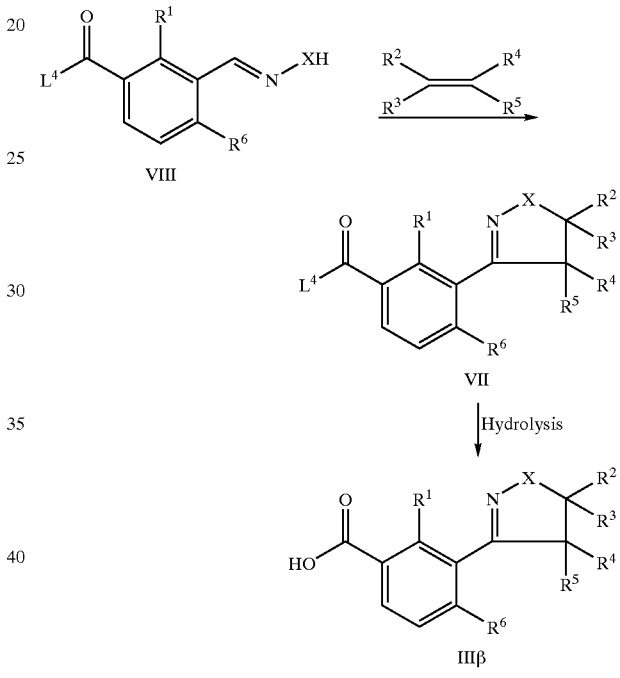

However, the benzoic acids IIIβ can also be obtained by converting an oxime or hydrazone of the formula IX into the corresponding nitrile oxides or nitrileimines and reacting these with alkenes to give the corresponding cycloaddition products (cf., for example, Chem. Ber. 106, 3252–3274 (1973)). Thus, for example, the oxime of the formula IX (X=O) is oxidized with sodium hypochlorite and reacted with a suitable alkene in an inert solvent such as methylene chloride, chloroform, tetrahydrofuran, dioxane or acetonitrile. The product is then, in the presence of a catalyst and a base, converted into the benzoic acid IIIβ using carbon monoxide and water.

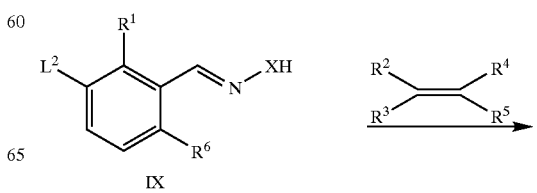

-continued

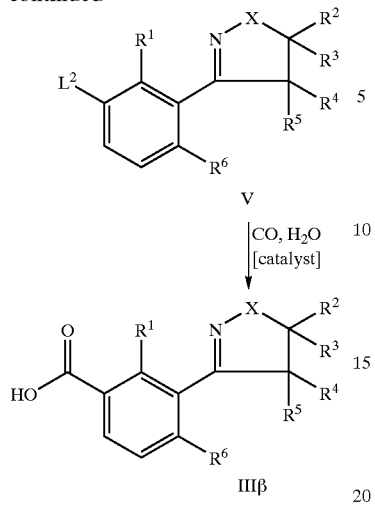

$L^2$ is a leaving group, such as halogen, for example chlorine, bromine or iodine, or sulfonate, such as mesylate or triflate; preference is given to bromine or triflate.

With respect to the carbonylation reaction, what has been said above applies analogously.

PREPARATION EXAMPLES

4-[2-Chloro-3-(4,5-dihydroisoxazol-3-yl)-4-methylsulfonylbenzoyl]-5-hydroxy-1-(1,1-dimethyl-1-ethyl)-1H-pyrazole (Compound 2.1)

2.32 g (0.02 mol) of 1-(1,1-dimethyl-1-ethyl)-5-hydroxy-1H-pyrazole and 2.3 g (0.02 mol) of potassium carbonate were added to a solution of 5.4 g (0.02 mol) of 2-chloro-3-(4,5-dihydroisoxazol-3-yl)-4-methylsulfonylbenzoyl chloride in 100 ml of ethylene glycol dimethyl ether, and the mixture was stirred overnight. The mixture was subsequently refluxed for 3 hours, the solvent was distilled off, the residue was taken up in 300 ml of water and washed with methylene chloride and the aqueous phase was acidified to pH=3 using 10% strength hydrochloric acid. The precipitate was filtered off with suction and dried at 400° C. This gave 4.6 g (65% of theory) of 4-[2-chloro-3-(4,5-dihydroisoxazol-3-yl)-4-methylsulfonylbenzoyl]-5-hydroxy-1-(1,1-dimethyl-1-ethyl)-1H-pyrazole].

In addition to the above compound, Table 2 lists other 3-(heterocyclyl)-substituted benzoylpyrazoles of the formula I which were prepared or are preparable in a similar manner.

TABLE 2

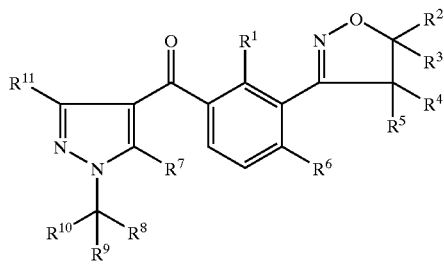

I where X = O

| No. | $R^1$ | $R^2$ | $R^3$ | $R^4$ | $R^5$ | $R^6$ | $R^7$ | $R^8$ | $R^9$ | $R^{10}$ | $R^{11}$ | physical data m.p. [° C.] $^1$H—NMR [δ in ppm] |
|---|---|---|---|---|---|---|---|---|---|---|---|---|
| 2.1 | Cl | H | H | H | H | SO$_2$CH$_3$ | OH | CH$_3$ | CH$_3$ | CH$_3$ | H | 198–200 |
| 2.2 | Cl | H | H | H | H | SO$_2$CH$_3$ | OH | CH$_3$ | CH$_3$ | H | H | 210–215 |
| 2.3 | Cl | H | H | H | H | SO$_2$CH$_3$ | OCH(CH$_3$)$_2$ | CH$_3$ | CH$_3$ | H | H | 175–180 |
| 2.4 | Cl | H | H | H | H | SO$_2$CH$_3$ | OCH$_2$CH$_3$ | CH$_3$ | CH$_3$ | H | H | 150–155 |
| 2.5 | Cl | H | H | H | H | SO$_2$CH$_3$ | OCH$_3$ | CH$_3$ | CH$_3$ | H | H | 185–190 |
| 2.6 | Cl | H | H | H | H | SO$_2$CH$_3$ | OCO[3-F—C$_6$H4] | CH$_3$ | CH$_3$ | H | H | 225–230 |
| 2.7 | Cl | H | H | H | H | SO$_2$CH$_3$ | OCOC$_6$H$_5$ | CH$_3$ | CH$_3$ | H | H | 220–225 |
| 2.8 | Cl | H | H | H | H | SO$_2$CH$_3$ | OCO[3,5-F$_2$—C$_6$H$_3$] | CH$_3$ | CH$_3$ | H | H | 220–225 |
| 2.9 | Cl | H | H | H | H | SO$_2$CH$_3$ | OH | CH(CH$_3$)$_2$ | CH$_3$ | H | H | 150–155 |
| 2.10 | Cl | H | H | H | H | SO$_2$CH$_3$ | OCH(CH$_3$)$_2$ | CH(CH$_3$)$_2$ | CH$_3$ | H | H | 125–130 |
| 2.11 | Cl | H | H | H | H | SO$_2$CH$_3$ | OCOC$_6$H$_5$ | CH(CH$_3$)$_2$ | CH$_3$ | H | H | 135–140 |
| 2.12 | Cl | H | H | H | H | SO$_2$CH$_3$ | OCO[3-F—C$_6$H$_4$] | CH(CH$_3$)$_2$ | CH$_3$ | H | H | 130–135 |
| 2.13 | OCH$_3$ | H | H | H | H | SO$_2$CH$_3$ | OH | CH$_3$ | CH$_3$ | H | H | 154–156 |
| 2.14 | OCH$_3$ | H | H | H | H | SO$_2$CH$_3$ | OCOSCH$_3$ | CH$_3$ | CH$_3$ | H | H | oil |
| 2.15 | Cl | H | H | H | H | SO$_2$CH$_3$ | OH | CH(CH$_3$)$_2$ | CH(CH$_3$)$_2$ | H | H | 200–205 |
| 2.16 | Cl | H | H | H | H | SO$_2$CH$_3$ | OCH$_3$ | CH(CH$_3$)$_2$ | CH(CH$_3$)$_2$ | H | H | 65–70 |
| 2.17 | Cl | H | H | H | H | SO$_2$CH$_3$ | OC$_2$H$_5$ | CH(CH$_3$)$_2$ | CH(CH$_3$)$_2$ | H | H | oil |
| 2.18 | OCH$_3$ | H | H | H | H | SO$_2$CH$_3$ | OCO[3-F—C$_6$H$_4$] | CH$_3$ | CH$_3$ | H | H | 78–79 |

The 3-(heterocyclyl)benzoylpyrazole derivatives of the formula I and their agriculturally useful salts are suitable, both in the form of isomer mixtures and in the form of the pure isomers, as herbicides. The herbicidal compositions comprising compounds I control vegetation on non-crop areas very efficiently, especially at high rates of application. They act against broad-leaved weeds and harmful grasses in crops such as wheat, rice, maize, soya and cotton, without causing any significant damage to the crop plants. This effect is mainly observed at low rates of application.

Depending on the application method used, the compounds I, or the compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The compounds I, or the herbicidal compositions comprising them, can be used for example in the form of ready-to-spray aqueous solutions, powders., suspensions, also highly-concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended uses; in any case, they should guarantee a very fine distribution of the active compounds according to the invention.

The herbicidal compositions comprise a herbicidally effective amount of at least one compound of the formula I or an agriculturally useful salt of I, and auxiliaries which are customarily used for formulating of crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding together the active compounds with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to the NMR spectrum).

The following formulation examples illustrate the preparation of such formulations:

I. 20 parts by weight of the compound No. 2.2 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.8 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 2.8 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil.

Pouring the solution into 100,000 parts by weight of water and finely distributing it therein gives an aqueous dispersion which comprises 0.02% by weight of the active compound.

IV. 20 parts by weight of the active compound No. 2.2 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 2.8 are mixed with 97 parts by weight of finely divided kaolin. This gives a dust which comprises 3% by weight of the active compound.

VI. 20 parts by weight of the active compound No. 2.2 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active compound No. 2.8 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active compound No. 2.2 is dissolved in a mixture composed of 80 parts by weight of cyclohexanone and 20 parts by weight of Wettol® EM 31 (=nonionic emulsifier based on ethoxylated castor oil).

This gives a Stable Emulsion Concentrate

The herbicidal compositions or the compounds I can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The compound I application rates are from 0.001 to 3.0, preferably 0.01 to 1.0 kg/ha of active substance (a.s.), depending on the control target, the season, the target plants and the growth stage.

To widen the activity spectrum and to achieve synergistic effects, the 3-(heterocyclyl)benzoylpyrazole derivatives of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, also in the form of a mixture with other crop protection agents, for example together with agents for controlling pests or phytopathogenic fungi or bacteria. Also of interest is the miscibility with mineral salt solutions, which are employed for treating nutritional and trace-element deficiencies. Non-phytotoxic oils and oil concentrates may also be added.

USE EXAMPLES

The herbicidal activity of the 3-(heterocyclyl)benzoylpyrazole derivatives of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this is adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.25, 0.125 or 0.0625 kg of a.s. (active substance)/ha.

Depending on the species, the plants were kept at 10–25° C. or –35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were of the following species:

| Scientific name | Common name |
| --- | --- |
| *Chenopodium album* | lamb's-quarters |
| *Echinochloa crus-galli* | barnyard grass |
| *Ipomoea ssp.* | morning glory |
| *Polygonum persicaria* | lady's-thumb |
| *Setaria faberi* | giant foxtail |
| *Setaria eiridis* | green foxtail |

| Scientific name | Common name |
|---|---|
| *Sinapis alba* | white mustard |
| *Solanum nigrum* | black nightshade |

At application rates of 0.25 or 0.125 kg/ha, the compound 2.2 (Table 2) showed very good post-emergence action both against the harmful grasses barnyard grass and green foxtail and against the weeds lamb's-quarters, lady's-thumb and black nightshade. Furthermore, the compound 2.8 (Table 2) exhibited, under the abovementioned conditions, very good action against undesirable plants such as barnyard grass, giant foxtail, morning glory, white mustard and black nightshade.

We claim:

1. A 3(heterocyclyl)benzoylpyrazole derivative of the formula I

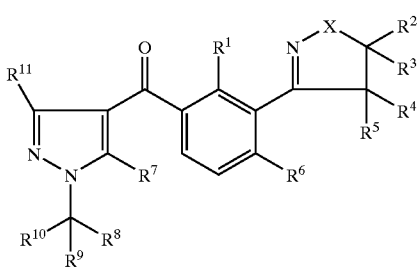

where

X is O, NH or $N(C_1-C_6-alkyl)$;

$R^1$ is nitro, halogen, $C_1-C_4$-alkoxy, $C_1-C_4$-haloalkoxy, $C_1-C_4$-alkylthio, $C_1-C_4$-haloalkylthio, $C_1-C_4$-alkylsulfonyl or $C_1-C_4$-haloalkylsulfonyl;

$R^2, R^3, R^4, R^5$ are hydrogen, $C_1-C_4$-alkyl or $C_1-C_4$-haloalkyl;

$R^6$ is halogen, nitro, $C_1-C_4$-haloalkyl, $C_1-C_4$-alkoxy, $C_1-C_4$-haloalkoxy, $C_1-C_4$-alkylthio, $C_1-C_4$-haloalkylthio, $C_1-C_4$-alkylsulfonyl or $C_1-C_4$-haloalkylsulfonyl;

$R^7$ is hydroxyl, $C_1-C_6$-alkoxy, $C_3-C_6$-alkenyloxy, $C_1-C_6$-alkylsulfonyloxy, $C_1-C_6$-alkylcarbonyloxy, $C_1-C_4$-(alkylthio)carbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1-C_4$-alkyl, $C_1-C_4$-haloalkyl, $C_1-C_4$-alkoxy or $C_1-C_4$-haloalkoxy;

$R^8, R^9$ are $C_1-C_4$-alkyl;

$R^{10}$ is hydrogen or $C_1-C_4$-alkyl;

where the number of the carbon atoms of the radicals $R^8, R^9$ and $R^{10}$ together is at most 7, $R^{11}$ is hydrogen or $C_1-C_4$-alkyl;

and its agriculturally useful salts.

2. A 3-(heterocyclyl)benzoylpyrazole derivative of the formula I as claimed in claim 1, where X is O;

$R^1$ is nitro, halogen, $C_1-C_4$-alkoxy or $C_1-C_4$-alkylthio;

$R^6$ is $C_1-C_4$-alkylthio or $C_1-C_4$-alkylsulfonyl.

3. A 3-(heterocyclyl)benzoylpyrazole derivative of the formula I as claimed in claim 1, where X is O;

$R^1$ is nitro, halogen, $C_1-C_4$-alkoxy or $C_1-C_4$-alkylthio;

$R^6$ is halogen, nitro, $C_1-C_4$-haloalkyl, $C_1-C_4$-alkoxy or $C_1-C_4$-haloalkoxy.

4. A 3-(heterocyclyl)benzoylpyrazole derivative of the formula I as claimed in claim 1, where X is $N(C_1-C_6-alkyl)$.

5. A process for preparing 3-(heterocyclyl) benzoylpyrazole derivatives of the formula I where $R^7$=hydroxyl, as claimed in claim 1, which comprises acylating a pyrazole of the formula II

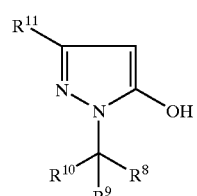

with an activated benzoic acid IIIα or a benzoic acid IIIβ

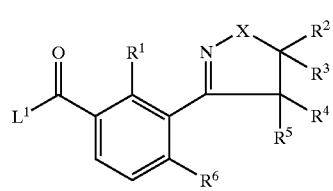

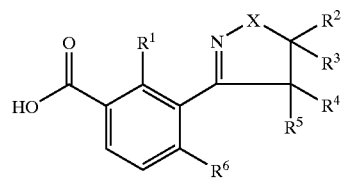

where the variables X, $R^1$ to $R^6$ and $R^8$ to $R^{11}$ are as defined in claim 1 and $L^1$ is a nucleophilically displaceable leaving group and rearranging acylation product, in the presence or absence of a catalyst, to give the compounds of the formula I where $R^7$=hydroxyl.

6. A process for preparing 3-(heterocyclyl) benzoylpyrazole derivatives of the formula I where $R^7$=OH, as claimed in claim 1, which comprises reacting a pyrazole of the formula II

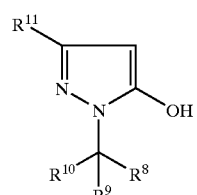

in which the variables $R^8$ to $R^{11}$ are as defined in claim 1, or an alkali metal salt thereof, with a 3-(heterocyclyl) benzene derivative of the formula V

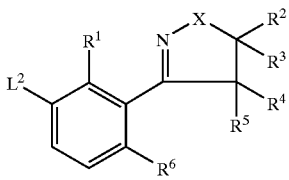

where the variables X and $R^1$ to $R^6$ are as defined in claim 1 and $L^2$ is a leaving group, in the presence of carbon monoxide, a catalyst and a base.

7. A process for preparing 3-(heterocyclyl) benzoylpyrazole derivatives of the formula I where $R^7$, hydroxyl, as claimed in claim 1, which comprises reacting a 3-(heterocyclyl)benzoylpyrazole derivative I where $R^7$=hydroxyl

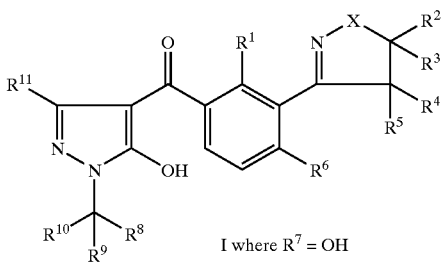

I where $R^7$ = OH with a compound of the formula VI $L^3$—$R^{7a}$ VI where $L^3$ is a nucleophilically displaceable leaving group;

$R^{7a}$ is $C_1$–$C_6$-alkyl, $C_3$–$C_6$-alkenyl, $C_1$–$C_6$-alkylsulfonyl, $C_1$–$C_6$-alkylcarbonyl, $C_1$–$C_4$-(alkylthio)carbonyl, phenylsulfonyl or phenylcarbonyl, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy.

8. A composition, comprising a herbicidally effective amount of at least one 3-(heterocyclyl)benzoylpyrazole derivative of the formula I or an agriculturally useful salt of I, as claimed in claim 1, and auxiliaries which are customarily used for formulating crop protection agents.

9. A process for preparing compositions as claimed in claim 8, which comprises mixing a herbicidally effective amount of at least one 3-(heterocyclyl)benzoylpyrazole derivative of the formula I or an agriculturally useful salt of I, and auxiliaries which are customarily used for formulating crop protection agents.

10. A method for controlling undesirable vegetation, which comprises allowing a herbicidally effective amount of at least one 3-(heterocyclyl)benzoylpyrazole derivative of the formula I or an agriculturally useful salt of I, as claimed in claim 1 to act on the plants, their habitat and/or on seed.

* * * * *